United States Patent
Wang et al.

(10) Patent No.: US 9,086,264 B2
(45) Date of Patent: Jul. 21, 2015

(54) POLARIZATION SENSITIVE SPECTRAL DOMAIN OCT USING AN INTERFERENCE SIGNAL MODULATED AT A CONSTANT FREQUENCY AND A TWO-PATH REFERENCE ARM WITH A SINGLE REFERENCE MIRROR

(75) Inventors: Ruikang Wang, Portland, OR (US); Chuanmao Fan, Shuangmiao Town (CN)

(73) Assignee: Oregon Health & Science University, Portland, OR (US)

( * ) Notice: Subject to any disclaimer, the term of this patent is extended or adjusted under 35 U.S.C. 154(b) by 770 days.

(21) Appl. No.: 12/602,822

(22) PCT Filed: Jun. 6, 2008

(86) PCT No.: PCT/US2008/066055
§ 371 (c)(1),
(2), (4) Date: Dec. 3, 2009

(87) PCT Pub. No.: WO2008/154349
PCT Pub. Date: Dec. 18, 2008

(65) Prior Publication Data
US 2010/0182609 A1    Jul. 22, 2010

Related U.S. Application Data
(60) Provisional application No. 60/942,278, filed on Jun. 6, 2007.

(51) Int. Cl.
*G01B 9/02* (2006.01)
*G01N 21/47* (2006.01)

(52) U.S. Cl.
CPC ........ *G01B 9/02044* (2013.01); *G01B 9/02028* (2013.01); *G01B 9/02078* (2013.01); *G01B 9/02091* (2013.01); *G01N 21/4795* (2013.01); *G01B 2290/70* (2013.01)

(58) Field of Classification Search
CPC .......... G01B 9/02028; G01B 9/02078; G01B 9/02044; G01B 9/02091; G01N 21/4795
USPC .................................. 356/479, 497, 491–495
See application file for complete search history.

(56) References Cited

U.S. PATENT DOCUMENTS

| | | | |
|---|---|---|---|
| 5,301,010 A * | 4/1994 | Jones et al. | .................... 356/479 |
| 5,861,952 A | 1/1999 | Tsuji et al. | |
| 6,198,540 B1 * | 3/2001 | Ueda et al. | .................... 356/479 |

(Continued)

FOREIGN PATENT DOCUMENTS

JP    2003337007 A    11/2003

OTHER PUBLICATIONS

Gotzinger, Erich et al., "High Speed Spectral Domain Polarization Sensitive Optical Coherence Tomography of the Human Retina," Optics Express, Dec. 12, 2005, vol. 13, No. 25, pp. 10217-10229.

(Continued)

*Primary Examiner* — Hwa Lee
(74) *Attorney, Agent, or Firm* — McDonnell Boehnen Hulbert & Berghoff LLP

(57) ABSTRACT

Embodiments include apparatuses and methods for spectral domain polarization sensitive optical coherence tomography including a reference assembly for detection of the polarization sensitive spectral interferograms formed by vertically and horizontally polarized beam components. Interference signals between the reference and sample beams may be modulated at a constant frequency.

11 Claims, 9 Drawing Sheets

(56) References Cited

U.S. PATENT DOCUMENTS

| | | | |
|---|---|---|---|
| 7,710,577 B2* | 5/2010 | Yatagai et al. | 356/492 |
| 7,982,881 B2* | 7/2011 | Fercher et al. | 356/497 |
| 8,049,899 B2* | 11/2011 | Waelti et al. | 356/497 |
| 2005/0140981 A1* | 6/2005 | Waelti | 356/479 |
| 2006/0072118 A1 | 4/2006 | Chan et al. | |
| 2008/0002183 A1* | 1/2008 | Yatagai et al. | 356/73 |
| 2008/0180683 A1* | 7/2008 | Kemp | 356/491 |
| 2009/0091766 A1* | 4/2009 | Hirose | 356/479 |

OTHER PUBLICATIONS

Yamanari, Masahiro et al., "Fiber-Based Polarization-Sensitive Fourier Domain Optical Coherence Tomography Using B-Scan-Oriented Polarization Modulation Method," Optics Express, Jul. 10, 2006, vol. 14, No. 14, pp. 6502-6515.

Hitzenberger, Christoph K. et al., "Measurement and Imaging of Birefringence and Optic Axis Orientation by Phase Resolved Polarization Sensitive Optical Coherence Tomography," Optics Express, Dec. 17, 2001, vol. 9, No. 13, pp. 780-790.

Baumann, Bernhard et al., "Single Camera Based Spectral Domain Polarization Sensitive Optical Coherence Tomography," Optics Express, Feb. 5, 2007, vol. 15, No. 3, pp. 1054-1063.

Cense, Barry et al., "Polarization-Sensitive Spectral-Domain Optical Coherence Tomography Using a Single Line Scan Camera," Optics Express, Mar. 5, 2007, vol. 15, No. 5, pp. 2421-2431.

* cited by examiner (A)　　　　　(B)

POLARIZATION SENSITIVE SPECTRAL DOMAIN OCT USING AN INTERFERENCE SIGNAL MODULATED AT A CONSTANT FREQUENCY AND A TWO-PATH REFERENCE ARM WITH A SINGLE REFERENCE MIRROR

CROSS-REFERENCE TO RELATED APPLICATIONS

The present application claims priority to U.S. Provisional Patent Application No. 60/942,278, entitled "Method and Apparatus for Localized Polarization Sensitive Imaging," filed Jun. 6, 2007, the entire disclosure of which is hereby incorporated by reference in its entirety for all purposes, except for those sections, if any, that are inconsistent with this specification.

TECHNICAL FIELD

Embodiments relate generally to the field of biomedical imaging, specifically to methods, apparatuses, and systems associated with optical coherence tomographic imaging.

BACKGROUND

Optical coherence tomography (OCT) is a non-invasive, three-dimensional (3-D) imaging technique, capable of optical ranging within a highly scattering sample, such as biological tissue. The development of polarization sensitive (PS) OCT has enabled OCT to sense the birefringence properties of biological tissue that are not provided by conventional OCT. Spectral domain (SD) OCT may provide further advantages because of the significant sensitivity and imaging speed advantages over time domain OCT. Current techniques, however, may not be capable of producing images of sufficient depth or clarity. Furthermore, conventional methods may require burdensome calibration steps for producing the desired images.

BRIEF DESCRIPTION OF THE DRAWINGS

Embodiments will be readily understood by the detailed description in conjunction with the accompanying drawings. Embodiments are illustrated by way of example and not by way of limitation in the figures of the accompanying drawings.

DETAILED DESCRIPTION OF DISCLOSED EMBODIMENTS

In the following detailed description, reference is made to the accompanying drawings which form a part hereof and in which is shown by way of illustration various embodiments. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding the disclosed embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of the disclosed embodiments.

The description may use the phrases "in an embodiment," or "in embodiments," which may each refer to one or more of the same or different embodiments. Furthermore, the terms "comprising," "including," "having," and the like, as used with respect to disclosed embodiments, are synonymous.

A phrase in the form of "N B" or in the form "A and/or B" means "(A), (B), or (A and B)." A phrase in the form "at least one of A, B and C" means "(A), (B), (C), (A and B), (A and C), (B and C) or (A, B and C)." A phrase in the form "at least one of A, B, and C" means "(A), (B), (C), (A and B), (A and C), (B and C), or (A, B and C)." A phrase in the form "(A) B" means "(B) or (A B)," that is, A is optional.

In various embodiments, methods, apparatuses, and systems for imaging, such as biomedical imaging, are provided. In exemplary embodiments, a computing system may be endowed with one or more components of the disclosed apparatuses and/or systems and may be employed to perform one or more methods as disclosed herein.

In an embodiment, there is provided an apparatus comprising a first light path configured to receive a first reference light beam and form, from the first reference light beam, a horizontally-polarized light beam; a second light path configured to receive a second reference light beam and form, from the second reference light beam, a vertically-polarized light beam; and a reference mirror configured to modulate, at a constant modulation frequency, an interference signal formed by the horizontally- and vertically-polarized light beams and the sample beam.

According to various embodiments, a spectral domain polarization sensitive optical coherence tomography (SD-PSOCT) system having a single-camera configuration may comprise a reference arm assembly (hereinafter "reference assembly") for polarization sensitive imaging. Although other applications are envisioned, the disclosed embodiments may be particularly suitable for in vitro and in vivo imaging.

Figure 1:
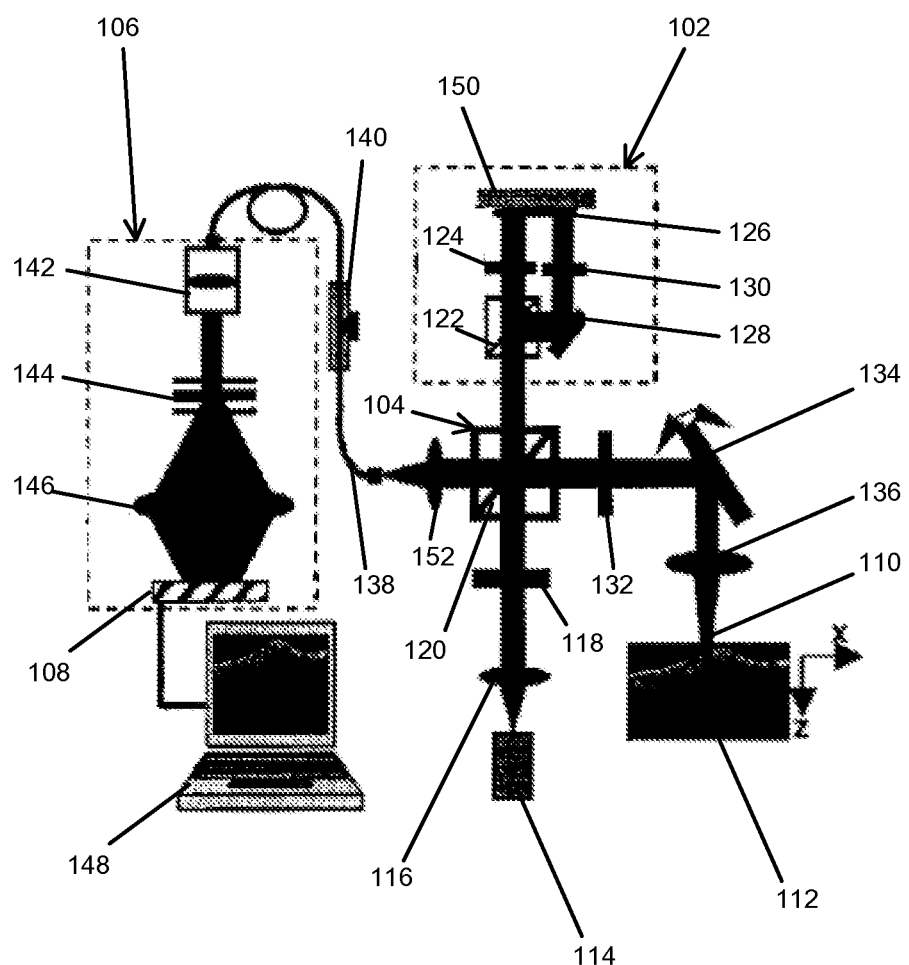
FIG. 1 illustrates an SD-PSOCT system in accordance with various embodiments.

An exemplary SD-PSOCT system including a reference assembly 102 is illustrated in FIG. 1. As illustrated, the exemplary reference assembly 102 may be configured to operatively couple to an interferometer 104 and a spectrometer 106 including a single charge-coupled device camera (CCD) 108 for spectral interferogram detection to perform polarization sensitive imaging. According to various embodiments, the reference assembly 102 may be configured to separate by a fixed distance OCT images from orthogonal polarization channels at the output plane of Fourier space by introducing a constant frequency modulation in the spatial varying spectral interferograms when a probe beam, provided by a probe 110, is swept over a sample 112. Because the orthogonally polarized beam components travel in the identical beam path in the spectrometer 106, the distortion between spectra may be avoided. Further, because the beam components travel together, calibration of the beams to achieve pixel-by-pixel correspondence may be unnecessary.

Still referring to FIG. 1, the exemplary reference assembly 102 may be configured to receive light from a light source 114 such as, for example, a broadband superluminescent diode (SLD). Although any light source suitable for the purpose may be enlisted for light source 114, an exemplary light source may be an SLD with a central wavelength of about 850 nm and full-width half-maximum (FWHM) bandwidth of about 30 nm, yielding a measured axial resolution of about 12 pm in air. For various other embodiments, the light source 114 may be a swept laser source, rather than the SLD. In embodiments of an SD-PSOCT system including a swept laser source, the spectrometer 106 may be replaced by an ultra-fast photodiode detector. For various embodiments, an SD-PSOCT system including a swept laser source as the light source 114 and photodiode for detection may perform substantially similarly to embodiments including an SLD as the light source 114 and the spectrometer 106 for detection.

Light from the light source 114 may be collimated by one or more lenses 116. According to various embodiments, the diameter of the collimated light may be about 3 mm.

Light from the light source 114 may be vertically polarized by a linear polarizer 118 and introduced to a polarization sensitive low coherence interferometer 104 including a beam splitter 120. The vertically-polarized light leaving the interferometer 104 (hereinafter "reference light") may then be delivered to the reference assembly 102 and the sample 112.

According to various embodiments, the reference light delivered to the reference assembly 102 may be split by a non-polarization beam splitter 122 into two substantially equal beams. One of the beams ("first beam") may pass through a quarter wave plate 124. The quarter wave plate 124 may have a fast axis oriented at 45°. The first beam may then be reflected by a staggered reference mirror 126. The first beam may then pass again through plate 124 to become a horizontally polarized beam. The other beam ("second beam") split by the non-polarization beam splitter 122 may be bent by another mirror 128 and reflected back by the staggered reference mirror 126 to join with the horizontally polarized beam. The joined beam may then be routed back into the interferometer 104.

In various embodiments, an SD-PSOCT system described herein may include one or more optical fiber couplers in addition to or instead of a beam splitter. So, in various embodiments, one or both of the beam splitters 120 and 122 may instead be an optical fiber coupler, depending on the particular desired application.

The reference assembly 102 may include a neutral density filter 130 placed in one or both of the first and second beam paths. The neutral density filter 130 may ensure that the light for two orthogonally polarized beam components (horizontal and vertical) impinged onto the CCD 108 has substantially equal strength. With such design, the reference assembly 102 may provide a fixed optical pathlength difference (OPD) between these two orthogonally polarized lights. The fixed OPD may be adjusted according to the needs for different applications. For example, according to various embodiments, the OPD between the vertically and horizontally polarized lights may be adjusted to about 2.0 mm. Because the orthogonally polarized beam components travel in the identical beam path in the spectrometer 106, the OCT images formed by the two orthogonally polarized beam components at the output plane of Fourier space may be separated after processing the mixed spectral interferograms captured by the CCD 108 (as described more fully herein).

As noted above, light from the polarization sensitive low coherence interferometer 104 may also be delivered to the sample 112 (hereinafter "sample light"). The sample light may pass through a quarter wave plate 132. The quarter wave plate 132 may have a fast axis oriented at 45° to transform the sample light into circularly polarized light. The sample light may then be delivered to the sample 112 by an X galvanometer scanner 134 and an achromatic lens 136. According to various embodiments, the achromatic lens 136 may include any focal length suitable for the application. In some embodiments, for example, the focal length may be about 100 mm.

The sample light may be introduced to the sample by the probe 110. The theoretical lateral imaging resolution, depth of focus, power, and other parameters of the probe beam may be variously adjusted depending on the application. In an embodiment, for example, the probe beam may have a theoretical lateral imaging resolution of about 28 μm, a depth of focus of about 4.2 mm, and a power of about 0.6 mW.

The reference light returning from the reference arm 102 and the sample light returning from sample 110 may be recombined through a lens 152 and coupled into a single mode fiber 138 for introduction to the spectrometer 106. According to various embodiments, a polarization controller 140 may be used in the single mode fiber 138 for fine tuning the polarization states of light in the spectrometer system.

The spectrometer 106 may be variously configured to be suitable for the intended purpose(s). According to the illustrated embodiment, the spectrometer 106 comprises a collimator 142, a polarization-insensitive transmission grating 144, and an achromatic focusing lens 146. According to an exemplary embodiment, the spectrometer 106 may comprise a 30 mm focal length collimator 142, a 1200 lines/mm polarization-insensitive transmission grating 144, and an achromatic focusing lens 146 with 190 mm focal length. The CCD 108 may comprise a line scan charge-coupled device camera for capturing both orthogonally polarized beam components (i.e., horizontal and vertical components) in parallel. Although the spectrometer 106 may include any CCD suitable for the purpose, in an embodiment, the CCD 108 may comprise one having 1024 pixels, each about 14×14 microns in size and 12 bits in digital depth, and capable of a 53 kHz line rate.

According to various embodiments, the propagating beam paths for vertically and horizontally polarized light components are substantially identical in the spectrometer 106, and their spectra captured by the identical CCD pixel arrays in parallel. This may be particularly advantageous in that careful calibration of the spectral components on the CCD array may not be necessary. For various embodiments, the spectrometer 106 may be designed to have an imaging depth being the full depth in the Fourier space used for imaging (e.g., approximately 8.2 mm in air), rather than half of the space used in conventional SD-PSOCT systems.

According to various embodiments, the CCD 108 may be variously adjusted for imaging. For various embodiments, for example, the CCD integration time may be set at about 100 microseconds for imaging. The spectral data from the CCD 108 (e.g., 1024 pixels, A scan) may then be outputted to a computer 148 for access by a user. According to an exemplary embodiment, the image data is downloaded to the computer 148 using CAMERALINK™ and a high-speed frame grabber board (for example, PC1 1428, commercially available from National Instruments, USA). For an exemplary embodiment, the CCD line scan rate may be 10 kHz, the imaging speed may be limited by the output power of the light source used (about 5 mW), and the signal sensitivity of 100 dB may be measured at z=+0.5 mm and dropped to about 85 dB at z=+3.5 mm when the camera integration time is set at about 100 microseconds. In this example, the light energy in the reference arm 102 may be adjusted such that the maximum intensity on the linear CCD array detector achieved approximately 40% of the camera's saturation level for each polarization beam component, and the remaining 20% of the dynamic range of the camera may be available to fill up the polarization interference fringes.

In an embodiment, there is provided a system comprising a light source; a reference assembly including: a first light path configured to receive a first reference light beam from the light source and form, from the first reference light beam, a horizontally-polarized light beam; a second light path configured to receive a second reference light beam from the light source and form, from the second reference light beam, a vertically-polarized light beam; and a signal modulating device configured to modulate an interference signal formed by the horizontally- and vertically-polarized light beams and a sample light beam to give a constant modulation frequency; a sampling assembly configured to provide light from the light source to a sample to obtain the sample light beam; and a spectrometer configured to detect a spectral interferogram formed by the horizontally-polarized light beam, the vertically-polarized light beam, and the sample light beam.

In various embodiments, the modulation of the interferogram may also be provided by scanner 134 and reference mirror 150 may be maintained in one position. In an exemplary embodiment, scanner 134 may be configured such that the input signal is scanned with an offset reference to the pivot point.

Figure 2:
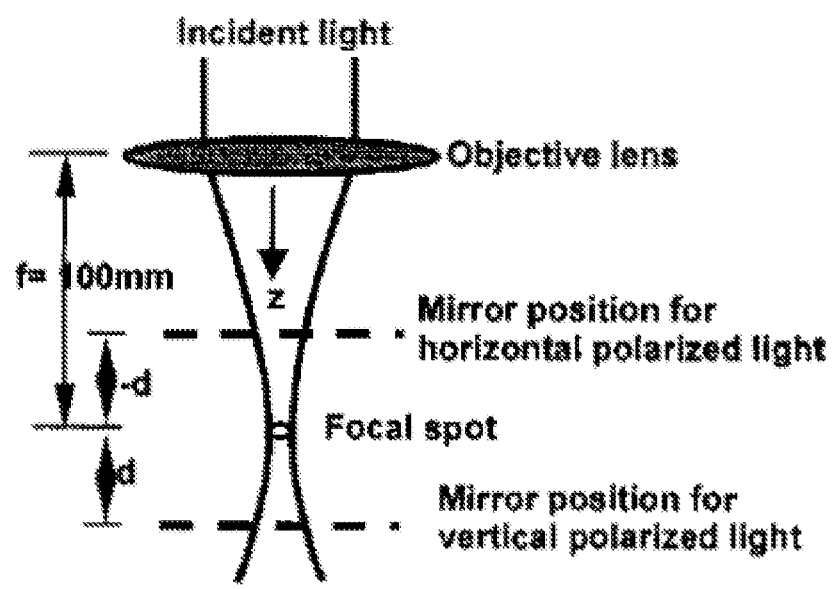
FIG. 2 illustrates an exemplary reference mirror in accordance with various embodiments.

Turning now to FIG. 2, with continuing reference to FIG. 1, illustrated is a depiction of the relationship between the focused sample beam and the effective positions for the reference mirror 126. Assuming that the coordinate origin along the depth direction, z, is at the focal spot, the optical fields in the reference arm 102 for the vertically and horizontally polarized lights may be expressed as:

$$E^r_V = R_V \exp[i2k(r-d)]; E^r_H = R_H \exp[i2k(r+d)]$$

(hereinafter "equation 1") where H and V refer to the signals from the horizontal and vertical polarization channels, R is the reflectivity in the reference arm 102, k is the wavenumber, and d is the distance of the reference mirror 126 position relative to the focal spot. In the sample arm (i.e., X galvanometer scanner 134, an achromatic lens 136, and probe 110), the optical fields that are decomposed into the vertically and horizontally polarized light may be expressed as:

$$E^s_V = \int S_V(z)\exp[i2k(z+r)]dz; E^s_H = \int S_H(z)\exp[i2k(z+r)]$$

(hereinafter "equation 2") where $S_{H,V}(z)$ represents the strengths of backscattering light at optical depth z in the sample in the respective polarization direction. Thus, considering that the vertically and horizontally polarized beam components are independent, the spectral interferogram detected at the CCD 108 may be described as:

$$I = |E^r_H + E^r_V + E^s_H + E^s_V|^2 = |E^r_H + E^s_H|^2 + |E^r_V + E^s_V|^2$$

(hereinafter "equation 3"). Because of the linear relationship between the contributions from different optical depth z from within a sample to equation 2, the problem of spectral interferogram detected by the CCD 108 at wavenumber k may be bundled and simplified by ignoring the terms that do not contribute to the useful signals, without loss of generosity, as:

$$I(k) = A_H(z)\cos[2k(z+d)+\phi_H(z)] + A_V(z)\cos[2k(z-d)+\phi_V(z)]$$

(hereinafter "equation 4") wherein $A_{H,V}(z)$ represents the magnitude of envelopes of interferograms formed by the respective polarization components and $\phi_{H,V}(z)$ is the random phase term that is due to the optical properties of the sample 112. Thus, the interferograms formed by the vertical and horizontal polarization light beams may be added together at the CCD 108.

According to various embodiments, the sample target may be placed near the zero phase delay line where the sensitivity may be the highest. This may be particularly desirable if the CCD 108 is insufficiently capable of digitizing the spectral components due to decreased sensitivity along the imaging depth. According to embodiments, OCT images formed by the two orthogonal polarization states may be placed side by side approximately centered at the zero delay line. For some embodiments, the images are placed about 2 mm apart.

According to various embodiments, spectral data captured by the CCD 108 may be used for deriving the spectral interference in the polarization sensitive interferometer 104. In embodiments wherein the spectral interferograms captured by the CCD 108 are real-valued components, Fourier transform thereof may produce a complex conjugate artifact mirroring the desired true sample image about the zero-phase delay in the entire complex space. For some embodiments, this may lead to un-resolved positive and negative distances. Accordingly, for various embodiments, an in vivo full-range complex Fourier domain OCT technique may be enlisted, such as the one described in U.S. Provisional Patent Application Ser. No. 60/826,998, filed Sep. 26, 2006 (incorporated herein by reference). In that disclosure, a constant modulation frequency was introduced into the spatial spectral interferograms when the probe beam, provided by the probe 110, is scanned over the sample 112. According to various embodiments, the reference mirror 126 in the reference arm 102 may be mounted onto a linear Piezo-translation stage 150. The Piezo-translation stage 150 may be configured to move the reference mirror 126 at a constant velocity across the B scan (i.e., x direction scan). Accordingly, in these embodiments, a constant modulation frequency $f_0$ is introduced into equation 4, $$I(k) = A_H(z)\cos[2k(z+d)+2\pi f_0 t+\phi_H(z)] + A_V(z)\cos[2k(z-d)+2\pi f_0 t+\phi_V(z)]$$

(hereinafter "equation 5") where t is the timing of the x scanner when it scans over the B scan, and t=0 is the start of the B scan. To eliminate the complex conjugate mirror images from the output plane of Fourier space, Hilbert transformation may be first applied to equation 5 against t to obtain the analytic function, $$\tilde{I}(k) = A_H(z)\exp\{i[2k(z+d)+2\pi f_0 t+\phi_H(z)]\} + A_V(z)\exp\{i[2k(z-d)+2\pi f_0 t+\phi_V(z)]\}$$

(hereinafter "equation 6").

A final Fourier transform against 2z may be used to retrieve the depth information of the sample 112 with the complex conjugate mirror terms removed from the output plane. The images formed by the vertically and horizontally polarized beam components may be separated by 2d around the zero delay line that is determined by embodiments of the reference assembly setup as described herein.

According to various embodiments, the modulation frequency introduced in the spectral interferograms may be set at 1.25 kHz with the CCD line rate set at 10 kHz. For these embodiments, because the introduced modulation frequency is one eighth of the data acquisition rate, the phenomenon on the spectral interference fringe washout at the CCD 108 may be ignored. For various embodiments, the OCT images formed by two orthogonally polarized beam components may be computed at once from discrete points measured in the x direction that make up a data matrix. In an exemplary embodiment, 1000 discrete points may be measured to form a data matrix of 1000 by 1024 elements (slice, B scan) from which the OCT images may be computed.

After the data has been acquired, post-processing may be performed. According to various embodiments, the average of A-lines may be subtracted from the raw data, followed by fixed pattern noise removal. This operation may effectively remove/minimize autocorrelation, self-cross correlation, and camera noise artifacts presented in the final images, which may improve the image quality. For various embodiments, the subtracted spectral interferograms may be converted into the equal frequency space by use of spline interpolation. In some embodiments, full range complex imaging processing may be applied to the processed data to remove the complex conjugate images presented in the Fourier output plane, leaving two OCT images side by side separated by 2d=2 mm as described herein. The two images may represent the images formed in the horizontal and vertical polarization channels, respectively. In still further embodiments, one of the images may be shifted by the fixed delay (e.g., 2.0 mm in embodiments described herein) to coincide with the other image. In the images, the A-scan signals of the object structure may be obtained in the form of $A_{H,V}(z)\exp[i\phi_{H,V}(z)]$. From the magnitude of envelopes $A_V(z)$ and $A_H(z)$ of interferograms, the depth-resolved retardation $\delta(z)$ may be expressed as:

$$\delta(z) = \arctan\left[\frac{A_V(z)}{A_H(z)}\right]$$

(hereinafter "equation 7") and depth-resolved reflectivity R(z) may be:

$$R(z) = \sqrt{A_V(z)^2 + A_H(z)^2}$$

(hereinafter "equation 8"). Since $A_V(z)$ and $A_H(z)$ may be determined by the amplitude of the sample electrical field rather than their phase, measurements of retardation and reflectivity may be substantially accurate. The fast axis direction $\theta(z)$ may be applicable to various embodiments and may be expressed as:

$$\theta(z) = \frac{\pi - [\Phi_V(z) - \Phi_H(z)]}{2}$$

(hereinafter "equation 9"). The measured values for $\delta(z)$ and $\theta(z)$ may be unambiguous in the range of 0° to 90° and 0° to 180°, respectively.

Figure 3:
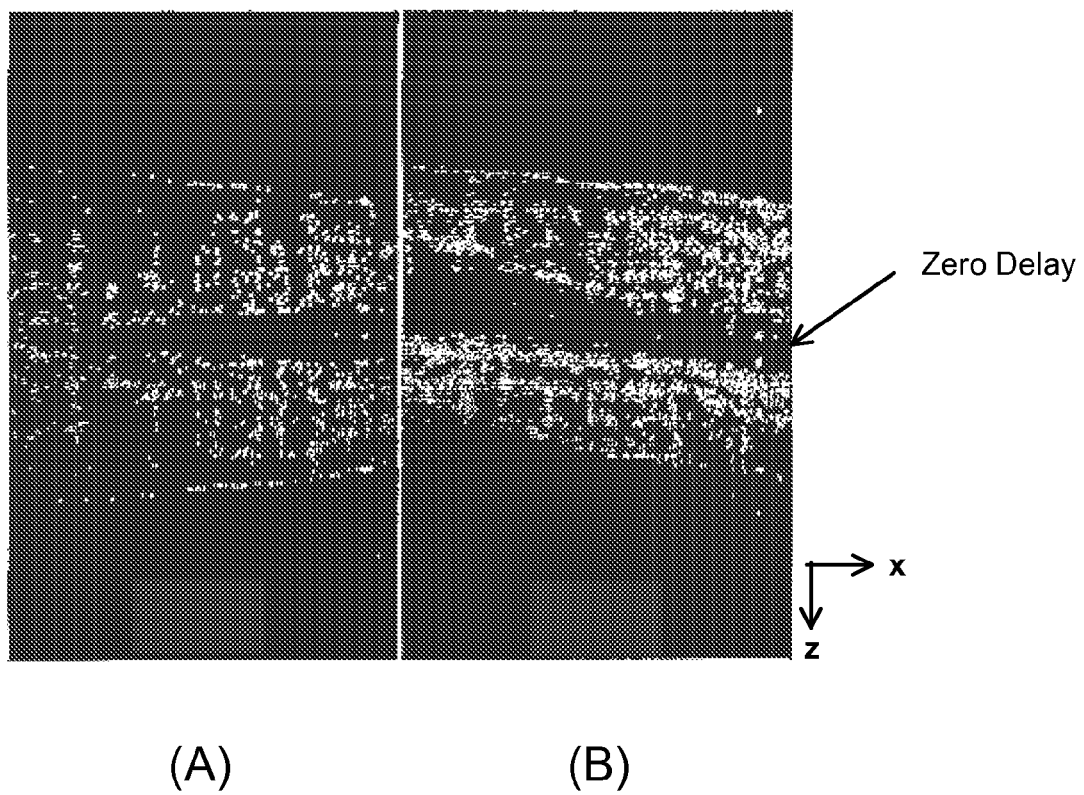
FIGS. 3(A) and 3(B) are images of a chicken breast acquired using an exemplary embodiment of an SD-PSOCT system in accordance with various embodiments.

Various embodiments of SD-PSOCT systems including a reference assembly may be capable of providing polarization sensitive imaging of various samples including, for example, various biological samples. Illustrated in FIGS. 3(A) and 3(B), for example, are exemplary in vitro results captured from a chicken breast sample. FIG. 3(A) shows the reconstructed in-depth OCT images formed by two orthogonal states of light by use of the standard FDOCT method. As expected, the disclosed reference assembly separates the images by about 2 mm centered at zero-delay line. However, due to the real-valued function of spectral interferograms captured by the CCD camera, the true image may be deteriorated by the overlapped complex conjugate image, which may result in the difficult or impossible separation of the two images formed by orthogonally polarized light. Shown in FIG. 3(B), however, the images are reconstructed by use of the full range complex imaging technique, i.e., modulation of the spectral interferograms across the B scan at a constant frequency induced by the movement of the reference mirror. As may be seen, full range complex imaging may be achieved with the complex conjugate image almost completely removed, where the image formed by the vertically polarized beam component is on the top of that formed by the horizontally polarized light. Accordingly, for various embodiments, polarization sensitive imaging may be possible by simply shifting one of the images with a known amount of optical delay in the depth direction (in this example, about 2.0 mm).

Figure 4:
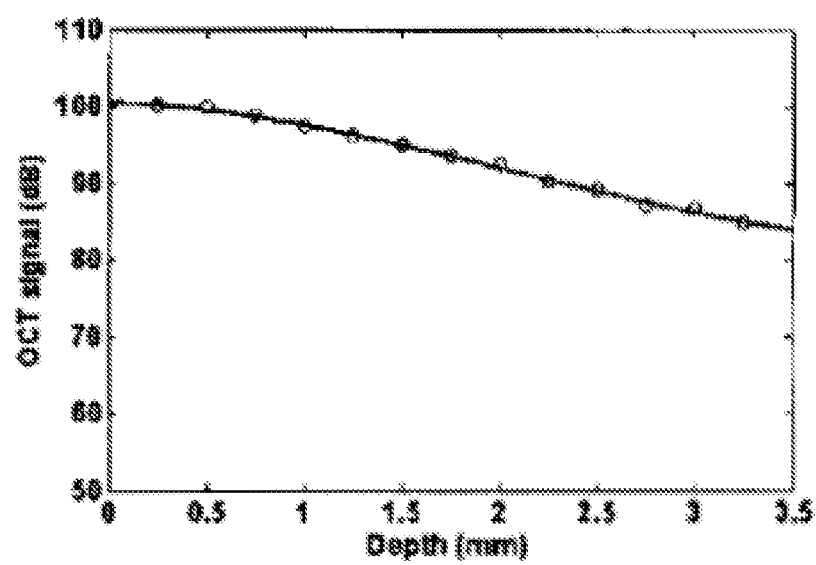
FIG. 4 is a plot of SD-PSOCT sensitivity against imaging depth in accordance with various embodiments.

Although the full range complex imaging technique may enable the OCT images formed by two orthogonal polarization beam components to be separated and centered about the zero delay line where the sensitivity of the spectrometer is highest, the sensitivity-falling-off characteristic of the system may continue to affect the final determination of the retardation values of the sample. Accurate determination of retardation using equation 7 may require the system sensitivity at corresponding depths of two images formed by orthogonal polarization beam components to be equal. For various embodiments, the measured curve of the system sensitivity may be used to retrospectively correct the OCT signals A(z) along the depth, applied for example to FIG. 3(B), so that the sensitivity along the depth may be approximately flat. FIG. 4 shows the system sensitivity (hollow circles on FIG. 4) measured along the depth up to 3.5 mm, where it may be seen that for the imaging depth near to the zero delay line, the sensitivity is about 100 dB and this value drops to about 85 dB at the depth of 3.5 mm. From the measured data, a correction curve may be obtained, c(z), by a polynomial curve fitting to a $2^{nd}$ order that may then normalized resulting in c(z) having a maximum value of unity (solid curve on FIG. 4). Thereafter, in various embodiments, the corrected OCT signals along the depth may be calculated by:

$$A'(z) = A(z)/c(z)$$

According to various embodiments and as described herein, one of the images may be shifted to coincide the two images formed by orthogonal polarization beam components, respectively, to obtain the depth-resolved retardation $\delta(z)$ and reflectivity R(z) (i.e., equations 7 and 8, respectively), without affecting the optic axis calculation of equation 9.

In an embodiment, there is provided a method comprising forming a horizontally-polarized light beam from a first reference light beam; forming a vertically-polarized light beam from a second reference light beam; forming an interference signal from the horizontally- and vertically-polarized light beams; and modulating the interference signal at a constant modulation frequency.

Figure 5:
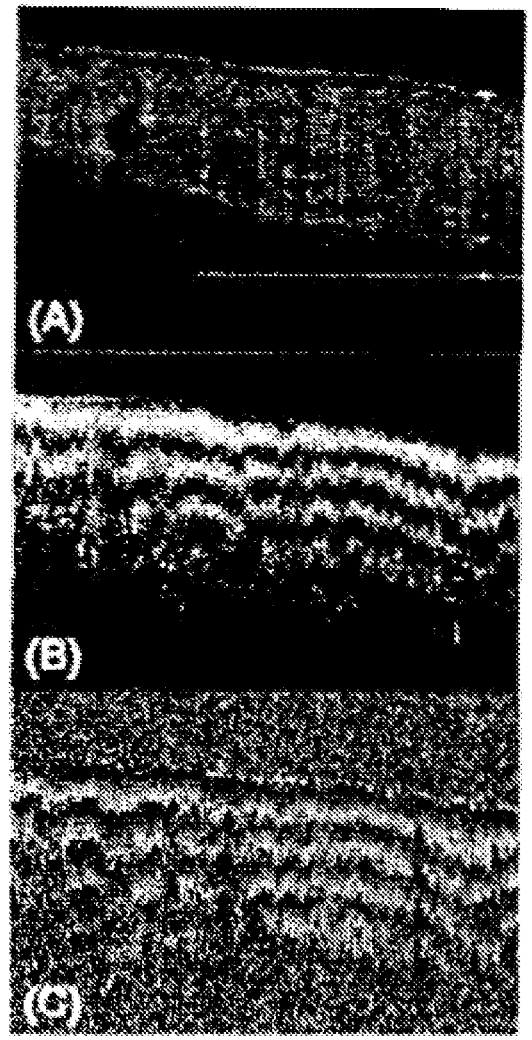
FIGS. 5(A), 5(B), and 5(C) are images of a chicken breast acquired using an exemplary embodiment of an SD-PSOCT system in accordance with various embodiments.

FIG. 5 shows exemplary final images resulting from various embodiments. For obtaining FIG. 5, a simple algorithm was used to find the surface of the sample, and then a signal band strip was isolated which stands for an optical length of about 2 mm from the surface. The signals in the other areas were forced to zero as there contains no useful OCT signals for calculation of the polarization sensitive images. FIG. 5(A)

gives the structural OCT image of the interrogated sample with the polarization artifact diminished. The straight-line shown is an artifact from the zero delay line that is a residue of the autocorrelation signal that was not completely removed by the pre-processing method. The presence of this artifact, however, may have a minimum effect on the interpretation of the sample. FIG. 5(B) is a cumulative round-trip phase retardation image. The phase retardation map of the sample is gray-scale coded from 0° to 90°. Because of the cumulative nature, it may appear to have periodic changes along the depth. The non-uniformity of the periodic phase appearance is not an artifact, but rather, may reveal certain organization information of the tissue components that make up the sample. The fast axis orientation image in FIG. 5(C) shows abrupt phase changes that are due to the phase wrapping effect because of the measured range lying between 0° and 180°.

For some embodiments, the separation distance between the two images formed by orthogonally polarized beam components and determined by the reference assembly design may limit the imaging depth that the system may achieve. For imaging most biological tissues, which are usually opaque (e.g., retina and skin, and also thin samples, such as human cornea), the separation distance of about 2 mm may be sufficient. For optical depths beyond about 2 mm, the OCT signals may rapidly fall into the noise floor. For relatively transparent biological samples, however, the separation distance may be increased by adjusting the reference assembly to increase the imaging depth.

For some embodiments wherein the two virtual reference mirrors are spaced about 2 mm apart, a relatively large depth of focus of the focusing sampling beam volume may be required to keep the system sensitivity as uniform as possible along the depth. In an embodiment, an objective lens with a focal length of about 100 mm giving a depth of focus of about 4.2 mm may be enlisted. This, however, may reduce the lateral imaging resolution that may be achieved. For various embodiments, an axicon lens may be used in the sample arm to focus the beam into the sample and to give an improved depth of focus while keeping the lateral resolution high.

Figure 6:
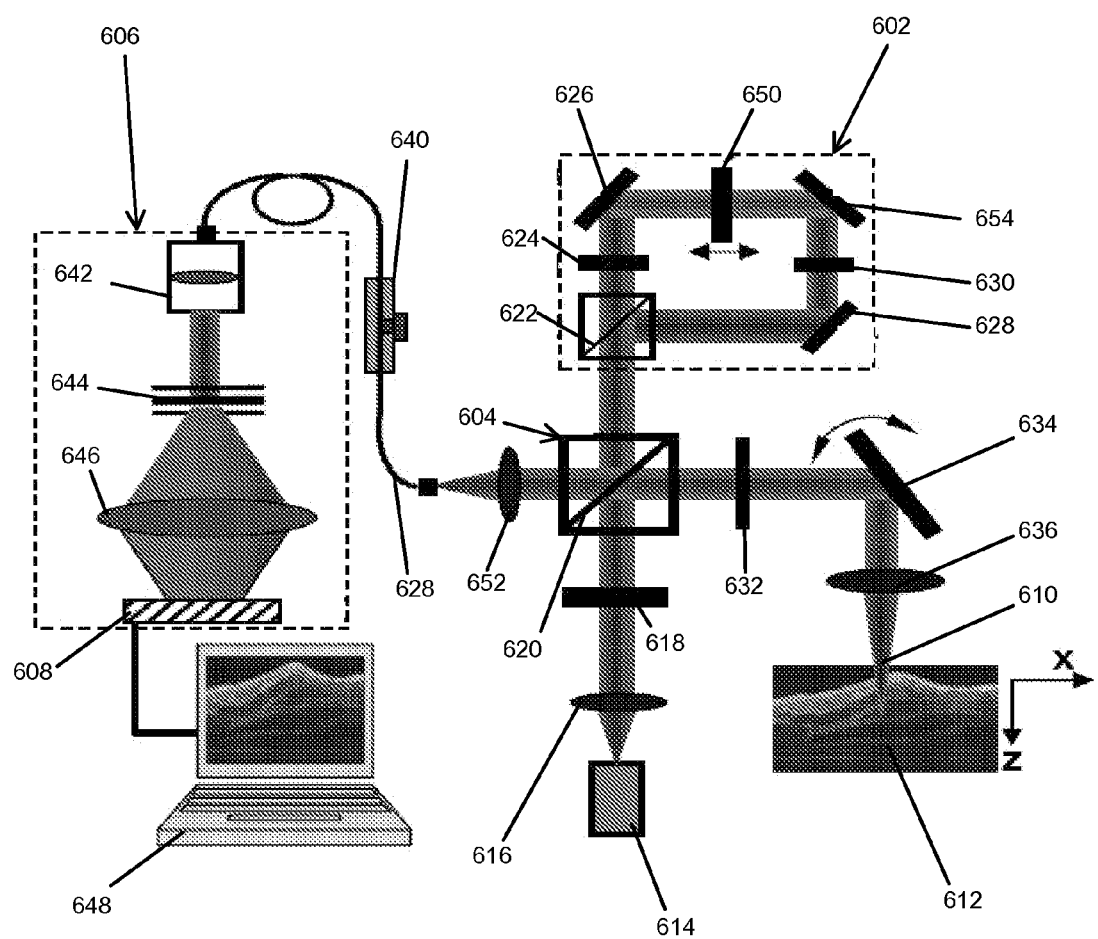
FIG. 6 illustrates another SD-PSOCT system in accordance with various embodiments.

Another exemplary SD-PSOCT system including a reference assembly 602 is illustrated in FIG. 6. As illustrated, the exemplary reference assembly 602 may include one or more of various features described herein for various other embodiments. For example, the illustrated embodiment, similarly to the embodiment illustrated in FIG. 1, may be configured to operatively couple to an interferometer 604 and a spectrometer 606 including a single charge-coupled device camera (CCD) 608 for spectral interferogram detection to perform polarization sensitive imaging. According to various embodiments, the reference assembly 602 may be configured to separate the OCT images formed by orthogonal polarization channels at the output plane of Fourier space by introducing a constant frequency modulation in the spatial varying spectral interferograms when a probe beam, provided by a probe 610, is swept over a sample 612. Because the orthogonally polarized beam components travel in the identical beam path in the spectrometer 606, the distortion between spectra may be avoided. Further, because the beam components travel together, calibration of the beams to achieve pixel-by-pixel correspondence may be unnecessary.

Still referring to FIG. 6, the exemplary reference assembly 602 may be configured to receive light from a light source 614. The light from the light source 614 may be collimated by one or more lenses 616 and vertically polarized by a linear polarizer 618. The light may then be introduced to a polarization sensitive low coherence interferometer 604 including a beam splitter 620. The vertically-polarized reference light leaving the interferometer may then be delivered to the reference assembly and to the sample 612.

According to various embodiments, the reference light delivered to the reference assembly 602 may be split by a non-polarization beam splitter 622 into two substantially equal beams. One of the beams ("first beam") may pass through a quarter wave plate 624. The quarter wave plate 624 may have, in some embodiments, a fast axis oriented at 45°. The first beam may then be bent by mirror 626 and reflected by a mobile reference mirror 650. The first beam may then pass again through the quarter wave plate 624 to become a horizontally polarized beam. The other beam ("second beam") may be bent by mirrors 628 and 654 and reflected back by the mobile mirror 650 to join with the horizontally polarized beam. The joined beam may then be routed back into the interferometer 604.

The reference assembly 602 may include a neutral density filter 630 placed in one or both of the first and second beam paths for ensuring that the light for the two orthogonally polarized beam components (horizontal and vertical) impinged onto the CCD 608 has substantially equal strength.

As noted above, light from the interferometer 604 may also be delivered to the sample 612 (hereinafter "sample light"). The sample light may pass through a quarter wave plate 632, and then may be delivered to the sample 612 by an X galvanometer scanner 634 and an achromatic lens 636. The sample light may be introduced to the sample by the probe 610.

The reference light returning from the reference arm 602 and the sample light returning from the sample 610 may be recombined through a lens 652 and coupled into a single mode fiber 638 for introduction to the spectrometer 606. According to various embodiments, a polarization controller 640 may be used in the single mode fiber 638 for fine tuning the polarization states of light in the spectrometer system.

The spectrometer 606 may be variously configured to be suitable for the intended purpose(s). The spectrometer 606 may comprise one or more of a collimator 642, a polarization-insensitive transmission grating 644, and an achromatic focusing lens 646. The spectral data from the CCD 608 may then be outputted to a computer 648 for access by a user.

Figure 7:
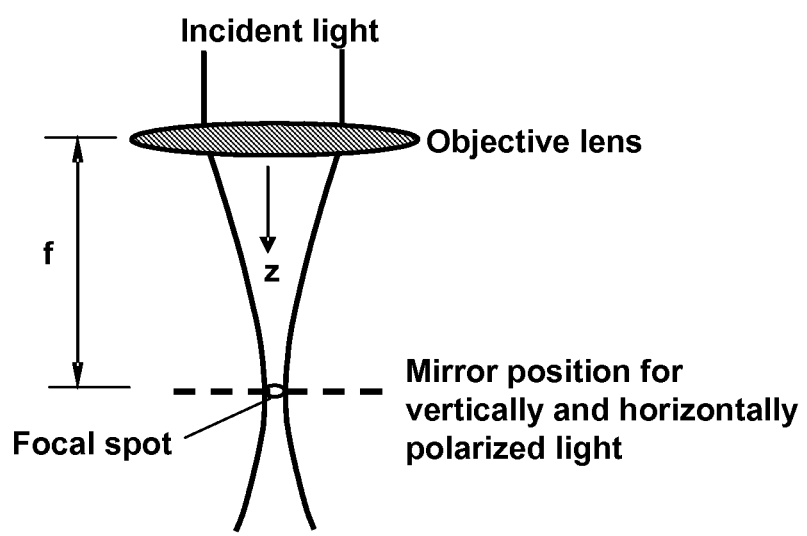
FIG. 7 illustrates another exemplary reference mirror in accordance with various embodiments.

Turning now to FIG. 7, illustrated is a depiction of the relationship between the focused sample beam and the effective positions for the mobile reference mirror. The same analysis described herein with reference to equations 1 to 4, in part or in whole, may be applied here, but with d=0. Consequently, equation 5 may be written as:

$$I(k)=A_H(z)\cos[2kx+2\pi f_0 t+\phi_H(z)]+A_V(z)\cos[2kz-2\pi f_0 t+\phi_V(z)]$$

(hereinafter "equation 10"). To eliminate the complex conjugate mirror images from the output plane of Fourier space, Hilbert transformation may be first applied to equation 10 against t to obtain the analytic function:

$$\tilde{I}(k)=A_H(z)\exp\{i[2kz+2\pi f_0 t+\phi_H(z)]\}+A_V(z)\exp\{i[-2kz-2\pi f_0 t+\phi_V(z)]\}$$

(hereinafter "equation 11").

A final Fourier transform against 2z may be used to retrieve the depth information of the sample with the complex conjugate mirror terms removed from the output plane. The images formed by the vertically and horizontally polarized beam components may be separated by and mirrored around the zero delay line that is determined by embodiments of the reference assembly setup as described herein.

Figure 8:
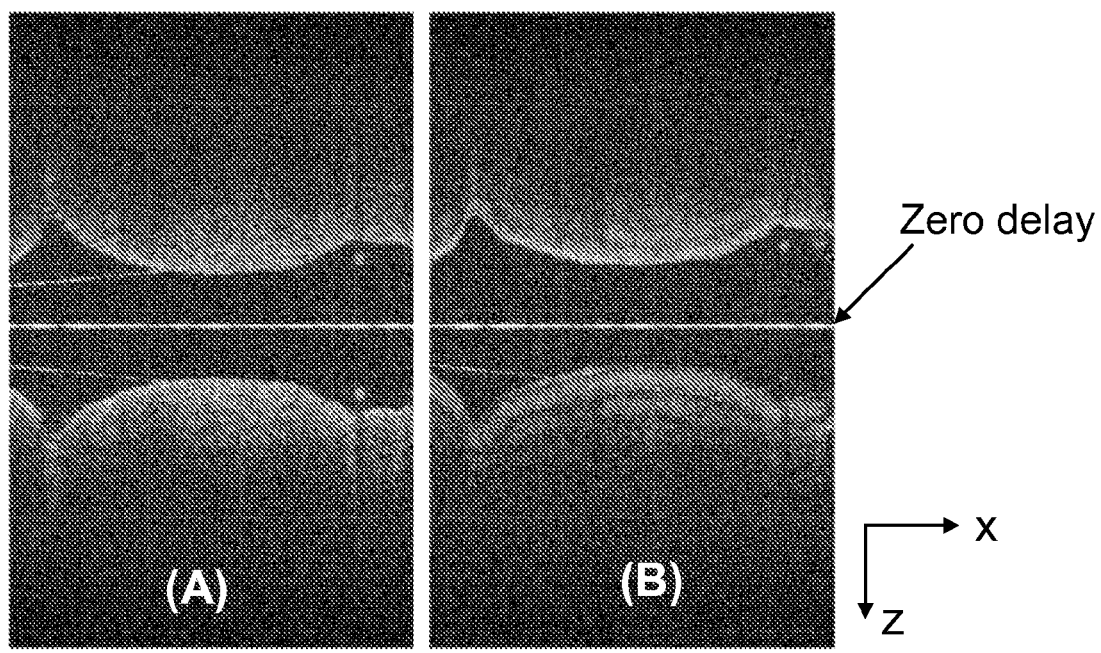
FIGS. 8(A) and 8(B) are images of a chicken breast acquired using an exemplary embodiment of an SD-PSOCT system in accordance with various embodiments.

Various embodiments of SD-PSOCT systems including a reference assembly may be capable of providing polarization sensitive imaging of various samples including, for example, various biological samples. Illustrated in FIGS. 8(A) and 8(B), for example, are exemplary in vitro results captured from a fresh chicken breast sample. FIG. 8(A) shows the reconstructed in-depth OCT images formed by two orthogonal states of light by use of the standard FDOCT method. As expected, the disclosed reference arm assembly separates the images mirrored by the zero-delay line. However, due to the real-valued function of spectral interferograms captured by the CCD camera, the true image may be deteriorated by the overlapped complex conjugate image, which may result in the difficult or impossible separation of the two images formed by orthogonally polarized light. Shown in FIG. 8(B), however, the images are reconstructed by use of the full range complex imaging technique, i.e., modulation of the spectral interferograms across the B scan at a constant frequency induced by the movement of the reference mirror. As may be seen, full range complex imaging may be achieved with the complex conjugate image almost completely removed, where the image formed by the vertically polarized beam component is in the negative space of the Fourier output plane, and that formed by the horizontally polarized light is in the positive space. Accordingly, for various embodiments, polarization sensitive imaging may be possible by simply flipping one of the images with respect to the zero delay line in the depth direction.

In various embodiments, the analytic function of the spectral interference of both orthogonally polarized lights as described in equation 6 and equation 11 may also be obtained by a Fourier filtering technique, rather than the Hilbert transformation described herein. The Fourier filtering technique may consist of Fourier transforming the spatial varying intereference signals, applying a windowing function in the Fourier space, and then inverse Fourier transforming back into spatial varying interference signals.

Figure 9:
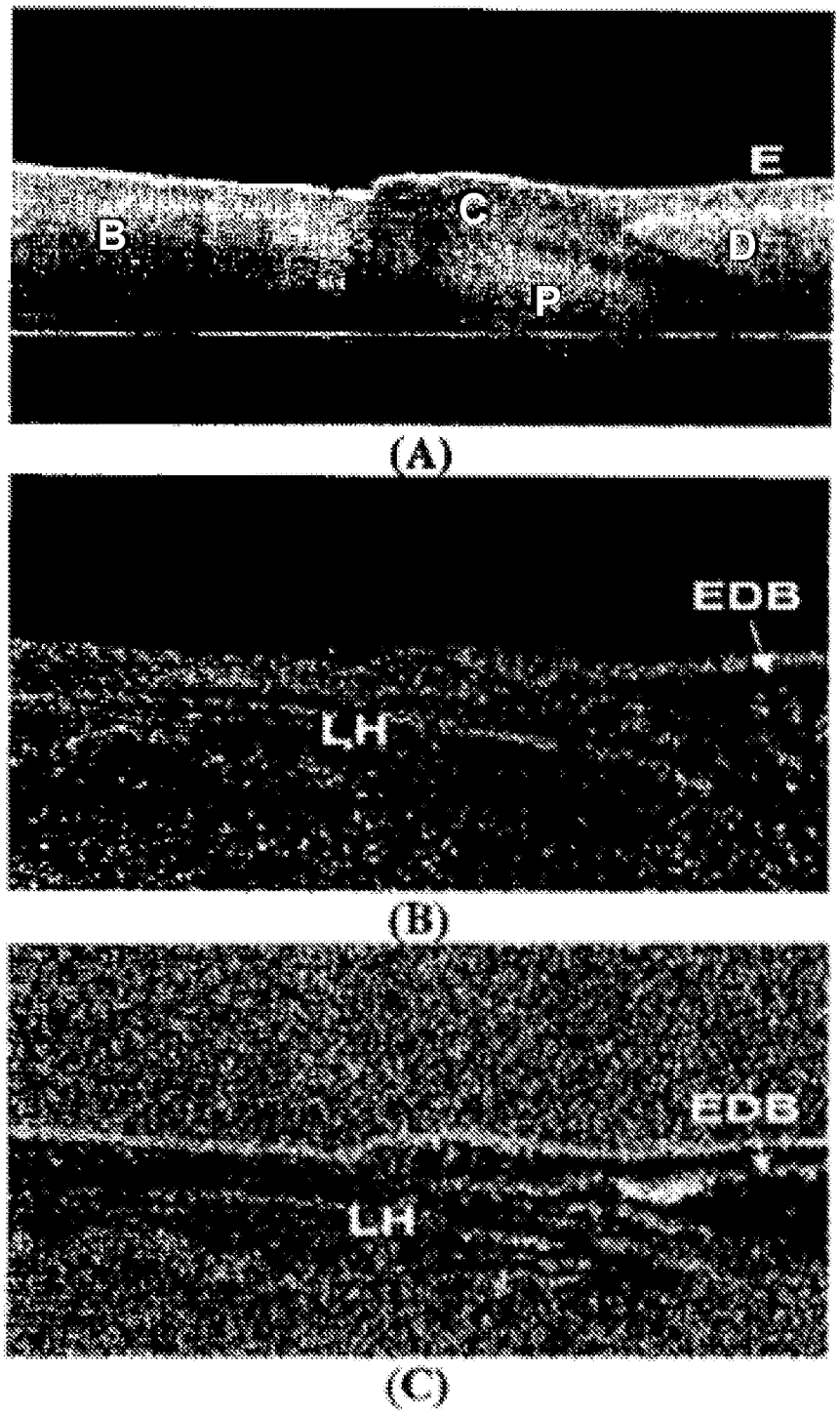
FIGS. 9(A), 9(B), and 9(C) are images of a human nail fold acquired using an exemplary embodiment of an SD-PSOCT system in accordance with various embodiments.

Various embodiments are suitable for use in in vivo applications. FIG. 9 shows various images captured from a proximal nail fold of a human volunteer using an exemplary embodiment of SD-PSOCT. For the embodiment, the scan covers an area of about 4 mm wide by about 1.3 mm deep (scaled by an average refractive index of about 1.35). The imaging rate was set at 10 frames per second with each frame covering 1000 A scans. The intensity image shown in FIG. 9(A) clearly delineates the epidermal (E) and dermal (D) regions near the nail fold, cuticle (C), nail plate (P), nail bed (B), and the lower half (LH) of the nail plate. The phase retardation image in FIG. 9(B) shows the highly birefringent property of the nail bed that gives banded structures as the amount of phase retardation wraps several times from 0° to 90°. At the epidermal-dermal boundary (EDB) of the nail fold, the transition from white to black may indicate that the light experiences a change in phase retardation angle with increasing depth due to the presence of birefringent tissue. The dermis region near to the nail fold appears homogeneous in the intensity image, whereas it shows structural appearance in the retardation image, indicating that the collagen fiber organization in this region is inhomogeneous. The same tissue properties observed in the retardation image are also evident in the fast axis orientation image as shown in FIG. 9(C).

Although certain embodiments have been illustrated and described herein for purposes of description of the preferred embodiment, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. An apparatus comprising:
   a first light path of a spectral domain optical coherence tomography (OCT) system reference arm through which a horizontally-polarized light beam passes;
   a second light path of the spectral domain OCT system reference arm through which a vertically-polarized light beam passes;
   a mobile reference mirror to reflect the horizontally-polarized light beam and the vertically-polarized light beam to form a joined beam with an optical pathlength difference between the horizontally-polarized light beam and the vertically-polarized light beam; and
   a signal modulation device that moves the mobile reference mirror at a constant velocity across a B scan to modulate, at a constant modulation frequency, an interference signal formed by the horizontally- and vertically-polarized light beams.

2. The apparatus of claim 1, further comprising a beam splitter to receive a source light beam and split the source light beam into a first reference light beam and a second reference light beam.

3. The apparatus of claim 2, wherein the beam splitter receives a vertically-polarized and/or a horizontally-polarized source light beam.

4. The apparatus of claim 1, wherein the first light path and the second light path have different path lengths to form the horizontally-polarized light beam and the vertically-polarized light beam with the optical pathlength difference, and wherein the optical pathlength difference is fixed.

5. The apparatus of claim 1, wherein the first light path includes a quarter wave plate.

6. The apparatus of claim 5, wherein the quarter wave plate includes a fast axis oriented at about 45°.

7. The apparatus of claim 1, wherein the signal modulation device is a linear moving stage and the reference mirror is affixed to the linear moving stage.

8. The apparatus of claim 7, wherein the interference signal formed by the horizontally- and vertically-polarized light beams is a spectral interferogram.

9. The apparatus of claim 1, wherein the first light path and/or the second light path includes a neutral density filter.

10. The apparatus of claim 1, further comprising:
    a light source to provide a first and a second reference light beams;
    a sampling assembly to provide light from the light source to a sample to obtain a sample light beam; and
    a spectrometer configured to detect a spectral interferogram formed by the horizontally-polarized light beam, the vertically-polarized light beam, and the sample light beam.

11. An apparatus comprising:
    a first light path of a spectral domain optical coherence tomography (OCT) system reference arm through which passes a horizontally-polarized light beam;
    a second light path of the spectral domain OCT system reference arm through which passes a vertically-polarized light beam;
    a reference mirror to reflect the horizontally-polarized light beam and the vertically-polarized light beam to form a joined beam with an optical pathlength difference between the horizontally-polarized light beam and the vertically-polarized light beam; and a signal modulation device that sweeps a sample light beam across a sample to introduce a constant modulation frequency for spatial varying spectral interferograms formed by the reflected horizontally- and vertically-polarized light beams.

* * * * *